United States Patent
Smith et al.

(10) Patent No.: US 12,292,451 B2
(45) Date of Patent: May 6, 2025

(54) ApoA1 EXCHANGE RATE ASSAYS IN SERUM

(71) Applicant: The Cleveland Clinic Foundation, Cleveland, OH (US)

(72) Inventors: Jonathan D. Smith, Shaker Heights, OH (US); Stanley L. Hazen, Pepper Pike, OH (US); Shuhui Wang Lorkowski, Shaker Heights, OH (US)

(73) Assignee: CLEVELAND CLINIC FOUNDATION, Cleveland, OH (US)

( * ) Notice: Subject to any disclaimer, the term of this patent is extended or adjusted under 35 U.S.C. 154(b) by 1000 days.

(21) Appl. No.: 15/734,631

(22) PCT Filed: Jun. 3, 2019

(86) PCT No.: PCT/US2019/035228
§ 371 (c)(1),
(2) Date: Dec. 3, 2020

(87) PCT Pub. No.: WO2019/236486
PCT Pub. Date: Dec. 12, 2019

(65) Prior Publication Data
US 2021/0231691 A1     Jul. 29, 2021

Related U.S. Application Data

(60) Provisional application No. 62/682,628, filed on Dec. 3, 2020.

(51) Int. Cl.
*G01N 33/92* (2006.01)
*G16H 15/00* (2018.01)
*G16H 50/30* (2018.01)

(52) U.S. Cl.
CPC ............ *G01N 33/92* (2013.01); *G16H 15/00* (2018.01); *G16H 50/30* (2018.01); *G01N 2333/775* (2013.01)

(58) Field of Classification Search
None
See application file for complete search history.

(56) References Cited

U.S. PATENT DOCUMENTS 9,494,606 B2 * 11/2016 Sacks ..................... G01N 33/92
2003/0100486 A1    5/2003 Ridker et al.
(Continued)

FOREIGN PATENT DOCUMENTS

WO    WO 2010/138899      12/2010

OTHER PUBLICATIONS

Wang et al., Supplement of ABCA1 mediates unfolding of apoA1 N-terminus on the cell surface prior to lipidation and release of nascent HDL, 2014, Arterioscler Thromb Vasc Biol., 33(6): supplement (Year: 2014).*

(Continued)

*Primary Examiner* — Lore R Jarrett
(74) *Attorney, Agent, or Firm* — Jason R. Bond; Casimir Jones, S.C.

(57) ABSTRACT

Provided herein are compositions, systems, kits, and methods for performing an apoA1 exchange assay to determine the risk of MACE and/or for conducting an action based on the assay results. In some embodiments, methods are provided for generating, or receiving, a report that graphically displays: i) the subjects ApoA1 exchange rate in a sample as lower than a control or threshold value, and ii) the subjects risk of a major adverse cardiac event (MACE) and/or cardiovascular disease as being higher than normal.

9 Claims, 10 Drawing Sheets

(56) References Cited

U.S. PATENT DOCUMENTS

| | | | |
|---|---|---|---|
| 2009/0035874 A1 | 2/2009 | Hazen et al. | |
| 2011/0070223 A1* | 3/2011 | Wolfert | A61K 31/22 435/11 |
| 2011/0245340 A1* | 10/2011 | Medford | A61P 9/00 435/15 |
| 2013/0108549 A1 | 5/2013 | Orser et al. | |
| 2014/0243233 A1* | 8/2014 | Altmann | G01N 33/6842 435/7.92 |
| 2015/0301070 A1 | 10/2015 | Meikle et al. | |
| 2015/0331000 A1* | 11/2015 | Collier | G01N 1/34 506/18 |
| 2015/0376704 A1* | 12/2015 | Harrington | G16H 50/20 702/19 |
| 2016/0024182 A1 | 1/2016 | Smith et al. | |
| 2016/0274134 A1* | 9/2016 | Mutharasan | G01N 33/542 |
| 2016/0305967 A1 | 10/2016 | Oda | |
| 2017/0336425 A1 | 11/2017 | Smith et al. | |
| 2018/0054152 A1* | 2/2018 | Leman | H02P 29/62 |
| 2018/0074080 A1* | 3/2018 | Thaxton | A61P 25/00 |

OTHER PUBLICATIONS

Lund-Katz et al., Kinetics and Mechanism of Free Cholesterol Exchange between Human Serum High- and Low-Density Lipoproteins, 1982, Biochemistry, 21, p. 2964-2969. (Year: 1982).*

International Search Report and Written Opinion for PCT/US2019/035228. Mailed Aug. 28, 2019. 12 pages.

Assmann et al., High-density lipoprotein cholesterol as a predictor of coronary heart disease risk. The PROCAM experience and pathophysiological implications for reverse cholesterol transport. Atherosclerosis. Jul. 1996;124 Suppl:S11-20.

Barter et al., Effects of torcetrapib in patients at high risk for coronary events. N Engl J Med. Nov. 22, 2007;357(21):2109-22.

Block et al., Effects of aspirin in combination with EPA and DHA on HDL-C cholesterol and ApoA1 exchange in individuals with type 2 diabetes mellitus. Prostaglandins Leukot Essent Fatty Acids. Nov. 2017;126:25-31.

Boden et al., Niacin in patients with low HDL cholesterol levels receiving intensive statin therapy. N Engl J Med. Dec. 15, 2011;365(24):2255-67.

Borja et al., HDL-apoA-I exchange: rapid detection and association with atherosclerosis. PLoS One. Aug. 28, 2013;8(8):e71541. 11 pages.

Borja et al., HDL-apolipoprotein A-I exchange is independently associated with cholesterol efflux capacity. J Lipid Res. Oct. 2015;56(10):2002-9.

Cavigiolio et al., Exchange of apolipoprotein A-I between lipid-associated and lipid-free states: a potential target for oxidative generation of dysfunctional high density lipoproteins. J Biol Chem. Jun. 11, 2010;285(24):18847-57.

Gordon et al., High density lipoprotein as a protective factor against coronary heart disease. The Framingham Study. Am J Med. May 1977;62(5):707-14.

Handa et al., Kinetic and thermodynamic analyses of spontaneous exchange between high-density lipoprotein-bound and lipid-free apolipoprotein A-I. Biochemistry. Feb. 3, 2015;54(4):1123-31.

Heier et al., Reduced HDL function in children and young adults with type 1 diabetes. Cardiovasc Diabetol. Jul. 6, 2017;16(1):85. 8 pages.

Khera et al., Cholesterol efflux capacity, high-density lipoprotein function, and atherosclerosis. N Engl J Med. Jan. 13, 2011;364(2):127-35.

Knapp et al., Clinical Epidemiology and Biostatistics. William and Wilkins, Harual Publishing Co. Malvern, Pa. 1992. TOC only. 7 pages.

Lincoff et al., Evacetrapib and Cardiovascular Outcomes in High-Risk Vascular Disease. N Engl J Med. May 18, 2017;376(20):1933-1942.

Neufeld et al., ApoA-I-Mediated Lipoprotein Remodeling Monitored with a Fluorescent Phospholipid. Biology (Basel). Jul. 12, 2019;8(3):53. 22 pages.

Rohatgi et al., HDL cholesterol efflux capacity and incident cardiovascular events. N Engl J Med. Dec. 18, 2014;371(25):2383-93.

Saleheen et al., Association of HDL cholesterol efflux capacity with incident coronary heart disease events: a prospective case-control study. Lancet Diabetes Endocrinol. Jul. 2015;3(7):507-13.

Sarzynski et al., Effects of Increasing Exercise Intensity and Dose on Multiple Measures of HDL (High-Density Lipoprotein) Function. Arterioscler Thromb Vasc Biol. Apr. 2018;38(4):943-952.

Schwartz et al., Effects of dalcetrapib in patients with a recent acute coronary syndrome. N Engl J Med. Nov. 29, 2012;367(22):2089-99.

Voight et al., Plasma HDL cholesterol and risk of myocardial infarction: a mendelian randomisation study. Lancet. Aug. 11, 2012;380(9841):572-80.

Wang et al., ABCA1 mediates unfolding of apolipoprotein AI N terminus on the cell surface before lipidation and release of nascent high-density lipoprotein. Arterioscler Thromb Vasc Biol. Jun. 2013;33(6):1197-205.

* cited by examiner

ApoA1 EXCHANGE RATE ASSAYS IN SERUM

The present application claims priority to U.S. Provisional application Ser. No. 62/682,628, filed Jun. 8, 2018, which is herein incorporated by references in its entirety.

STATEMENT REGARDING FEDERAL FUNDING

This invention was made with government support under grant number RO1 HL128268 awarded by the National Institutes of Health. The government has certain rights in the invention.

FIELD

Provided herein are compositions, systems, kits, and methods for performing an apoA1 exchange assay to determine the risk of MACE and/or for conducting an action based on the assay results. In some embodiments, methods are provided for generating, or receiving, a report that graphically displays: i) the subject's ApoA1 exchange rate in a sample as lower than a control or threshold value, and ii) the subject's risk of a major adverse cardiac event (MACE) and/or cardiovascular disease as being higher than normal.

BACKGROUND

Low levels of HDL-cholesterol (HDL-C) levels are associated with prevalent and incident risk for coronary heart disease, thus HDL-C has been called the "good cholesterol" (1, 2). However, drug trials targeting HDL-C as well as a genetic instrument called mendelian randomization have called into question whether low HDL is causal for MACE (3-7). As HDL is a major player in reverse cholesterol transport (RCT), the process of removing peripheral cholesterol to the liver for excretion into the bowel, the concept has emerged that it is low HDL function, rather than HDL-cholesterol, that is causal for MACE. Indeed, there is a growing literature that one HDL functional assay, the cholesterol efflux capacity (CEC) of apoB-depleted serum, is associated with both prevalent and incident MACE (8-10). However, the cholesterol efflux capacity assay requires cell culture and radioactivity, and it cannot be performed as a routine, relativity inexpensive, diagnostic assay.

SUMMARY

Provided herein are compositions, systems, kits, and methods for performing an apoA1 exchange assay to determine the risk of MACE and/or for conducting an action based on the assay results. In some embodiments, methods are provided for generating, or receiving, a report that graphically displays: i) the subject's ApoA1 exchange rate in a sample as lower than a control or threshold value, and ii) the subject's risk of a major adverse cardiac event (MACE) and/or cardiovascular disease as being higher than normal.

In some embodiments, provided herein are methods of determining the ApoA1 exchange rate in a sample and generating a report comprising: a) treating a sample from a subject to determine the subject's ApoA1 exchange rate; and b) generating a report (e.g., paper or electronic report) that graphically displays: i) the subject's ApoA1 exchange rate in the sample as: i) lower than a control value, and/or ii) lower than a threshold value of 0.85 (or 1.0, 0.95, 0.9, 0.8, or 0.7); and ii) the subject's risk of a major adverse cardiac event (MACE) and/or cardiovascular disease being higher than normal.

In certain embodiments, provided herein are methods of determining the ApoA1 exchange rate in a sample and generating a report comprising: a) contacting a sample from a subject with a lipid-free apoA1 reporter molecule to determine the subject's ApoA1 exchange rate, wherein the lipid-free apoA1 reporter is lipid-sensitive; and b) generating a report (e.g., paper or electronic report) that graphically displays: i) the subject's ApoA1 exchange rate in the sample as: i) lower than a control value, and/or ii) lower than a threshold value of 0.85 (or 1.0, 0.95, 0.9, 0.8, or 0.7); and ii) the subject's risk of a major adverse cardiac event (MACE) and/or cardiovascular disease being higher than normal.

In particular embodiments, provided herein are methods of receiving an ApoA1 exchange rate report and performing an action based thereon comprising: a) receiving a report (e.g., paper or electronic report) that graphically displays: i) a subject's ApoA1 exchange rate in a sample as: i) lower than a control value, and/or ii) lower than a threshold value of 0.85 (or 1.0, 0.95, 0.9, 0.8, or 0.7); and ii) the subject's risk of a major adverse cardiac event (MACE) and/or cardiovascular disease being higher than normal; and b) performing at least one of the following: i) performing coronary catheterization on the subject; ii) treating the subject with a cardiovascular disease (CVD) therapeutic, iii) prescribing the subject a CVD therapeutic, iv) performing at least one additional CVD diagnostic test on the subject, v) admitting and/or directing the subject to be admitted to a hospital, and vi) performing a stress test on the subject.

In certain embodiments, the report graphically displays the subject's ApoA1 exchange rate. In other embodiments, the report graphically displays the subject's ApoA1 exchange rate as less than the threshold value. In further embodiments, the subject's ApoA1 exchange rate is presented in a column on the report indicative of being lower than the threshold value. In some embodiments, the subject's ApoA1 exchange rate is presented in a color indicative of being lower than the threshold value. In additional embodiments, the report graphically displays the subject's ApoA1 exchange rate as less than the control value. In further embodiments, the subject's ApoA1 exchange rate is presented in a column indicative of being lower than the control value. In other embodiments, the subject's ApoA1 exchange rate is presented in a color indicative of being lower than the control value. In particular embodiments, the control value is based on the average ApoA1 exchange rate from a plurality of healthy individuals or a plurality of individuals without cardiovascular disease.

In some embodiments, provided herein are methods of detecting the risk of MACE and/or performing an action based on assay results comprising: a) contacting a sample from a subject with a lipid-free apoA1 reporter molecule to determine the level of ApoA1 exchange rate, wherein said lipid-free apoA1 reporter is lipid-sensitive, and b) determining the risk of MACE, or b) performing at least one of the following: i) performing coronary catheterization on the subject based on finding a low level of apoA1 exchange rate in said sample; ii) treating the subject with a cardiovascular disease (CVD) therapeutic (e.g., a statin, an ACE inhibitor, an aldosterone inhibitor, an angiotensin II receptor blocker, a beta-blocker, a calcium channel blockers, a cholesterol-lowering drug, Digoxin, a Diuretic, potassium, magnesium, a vasodilator, or Warfarin) based on finding a low level of apoA1 exchange in said sample, iii) prescribing the subject a CVD therapeutic based on finding a low level (e.g., compared to a control of a general population and/or a healthy population) of apoA1 exchange in said sample, iv) performing at least one additional diagnostic test on the subject based on finding a low level of apoA1 exchange in said sample, v) admitting and/or directing the subject to be admitted to a hospital based on finding a low level of apoA1 exchange in said sample, vi) discharging the subject from a treatment facility based on finding a high or normal level of apoA1 exchange (e.g., compared to a control of general population and/or healthy population) in said sample, and vii) performing a stress test on the subject based on finding a low level (e.g., compared to a control of a general population and/or a healthy population) of apoA1 exchange in said sample.

In some embodiments, provided herein are methods of detecting the risk of MACE and/or performing an action based on assay results comprising: a) determining the level of ApoA1 exchange rate in said sample, and b) performing at least one of the following: i) performing coronary catheterization on the subject based on finding a low level (e.g., compared to a control of a general population and/or a healthy population) of apoA1 exchange rate in said sample; ii) treating the subject with a cardiovascular disease (CVD) therapeutic (e.g., a statin, an ACE inhibitor, an aldosterone inhibitor, an angiotensin II receptor blocker, a beta-blocker, a calcium channel blockers, a cholesterol-lowering drug, Digoxin, a Diuretic, potassium, magnesium, a vasodilator, or Warfarin) based on finding a low level (e.g., compared to a control of a general population and/or a healthy population) of apoA1 exchange in said sample, iii) prescribing the subject a CVD therapeutic based on finding a low level (e.g., compared to a control of a general population and/or a healthy population) of apoA1 exchange in said sample, iv) performing at least one additional diagnostic test on the subject based on finding a low level (e.g., compared to a control of a general population and/or a healthy population) of apoA1 exchange in said sample, v) admitting and/or directing the subject to be admitted to a hospital based on finding a low level (e.g., compared to a control of a general population and/or a healthy population) of apoA1 exchange in said sample, vi) discharging the subject from a treatment facility based on finding a high level (e.g., compared to a control of a general population and/or a healthy population) of apoA1 exchange in said sample, vii) performing a stress test on the subject based on finding a low level (e.g., compared to a control of a general population and/or a healthy population) of apoA1 exchange in said sample, and viii) determining the risk of MACE for said subject. In particular embodiments, the determining comprising contacting said sample from a subject with a lipid-free apoA1 reporter molecule to determine the level of ApoA1 exchange rate, wherein said lipid-free apoA1 reporter is lipid-sensitive.

In certain embodiments, the lipid-free apoA1 reporter molecule comprises at least a portion of human ApoA1 protein. In other embodiments, the lipid-free apoA1 reporter molecule is fluorescently labeled. In additional embodiments, the lipid-free apoA1 reporter molecule only emits a detectable signal when it binds lipid. In some embodiments, the lipid-free apoA1 reporter is lipid sensitive. In further embodiments, the lipid-free apoA1 reporter comprises at least a portion of human ApoA1 that is doubly-labeled on free amines with a lipid sensitive labels (e.g., NBD (nitrobenzoxadiazole)) whose fluorescence increases in a hydrophobic environment, and a lipid insensitive label (e.g., Alexa647 on the lysine residue). In some embodiments, the lipid-free apoA1 reporter comprises bodipy TMR/Alexa647 ApoA1. In other embodiments, sample is serum, plasma, or whole blood.

DESCRIPTION OF THE FIGURES

FIG. 9. High apoA1 exchange rate is associated with decreased incident MACE. A. ApoA1 exchange rates were assayed in 997 serum samples obtained from a Cleveland Clinic cardiac catheterization cohort with 3 years follow-up. A Kaplan-Meier plot showed significantly lower MACE (major adverse cardiovascular events, defined as death, nonfatal myocardial infarction, or nonfatal stroke)-free survival in the high apoA1 exchange rate (top 75th percentile) group vs. the low apoA1 exchange rate (bottom 25th percentile). B. Forrest plot of the hazard ratios between apoA1 exchange rate and MACE shown for the high apoA1 exchange rate (top 75th percentile) normalized to the low apoA1 exchange rate group (bottom 25th percentile). Multilogistic regression models included either no adjustments or different adjustments Adjustment 1 is for age, sex, smoking, diabetes mellitus, hypertension; adjustment 2 adds MPO; adjustment 3 adds LDL-C, TG, statin, and aspirin onto adjustment 2; adjustment 4 adds HDL-C to adjustment 3; and adjustment 5 adds apoA1 levels to adjustment 3. The 5% to 95% confidence interval is indicated by line length.

DETAILED DESCRIPTION

Provided herein are compositions, systems, kits, and methods for performing an apoA1 exchange assay to determine the risk of MACE and/or for conducting an action based on the assay results. In some embodiments, methods are provided for generating, or receiving, a report that graphically displays: i) the subject's ApoA1 exchange rate in a sample as lower than a control or threshold value, and ii) the subject's risk of a major adverse cardiac event (MACE) and/or cardiovascular disease as being higher than normal.

In certain embodiments, ApoA1 exchange rate in the biological sample obtained from the test subject may compared to a control value. In certain embodiments, the subject's ApoA1 exchange rate is normalized to a serum pool composed of serum from healthy individuals or individuals without cardiovascular disease (e.g., prior to being compared to a control value).

A control value is an ApoA1 exchange rate that represents a known or representative rate. For example, the control value can be based upon the ApoA1 exchange rate in comparable samples obtained from a reference cohort. In certain embodiments, the reference cohort is the general population. In certain embodiments, the reference cohort is a select population of human subjects. In certain embodiments, the reference cohort is comprised of individuals who have not previously had any signs or symptoms indicating the presence of MACE, atherosclerosis, angina pectoris, history of an acute adverse cardiovascular event such as a myocardial infarction or stroke, evidence of atherosclerosis by diagnostic imaging methods including, but not limited to coronary angiography. In certain embodiments, the reference cohort includes individuals, who if examined by a medical professional would be characterized as free of symptoms of disease (e.g., cardiovascular disease). In another example, the reference cohort may be individuals who are nonsmokers (i.e., individuals who do not smoke cigarettes or related items such as cigars). A nonsmoker cohort may have a different normal ApoA1 exchange rate than will a smoking population or the general population. Accordingly, the control values selected may take into account the category into which the test subject falls. Appropriate categories can be selected with no more than routine experimentation by those of ordinary skill in the art.

The control value can take a variety of forms. The control value can be a single cut-off value, such as a median or mean. The control value can be established based upon comparative groups such as where the risk in one defined group is double the risk in another defined group. The control values can be divided equally (or unequally) into groups, such as a low risk group, a medium risk group and a high-risk group, or into quadrants, the lowest quadrant being individuals with the highest risk, and the other three quadrants with lower risk, and the test subject's risk of having CVD can be based upon which group his or her test value falls. Control ApoA1 exchange rates in biological samples obtained, such as mean levels, median levels, or "cut-off" levels, may be established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed.

The ApoA1 exchange rate in a subject's biological sample may be compared to a single control value or to a range of control values. If the level of ApoA1 exchange rate in the test subject's biological sample is less than the control value or is in the lower range of control values, the test subject is at greater risk of developing or having CVD or experiencing a major adverse cardiac event within the ensuing year, two years, and/or three years than individuals with levels comparable to or above the control value or in the higher range of control values. In contrast, if levels of the present risk predictor in the test subject's biological sample is above the control value or is in the higher range of control values, the test subject is at a lower risk of developing or having CVD or experiencing a major adverse cardiac event within the ensuing year, two years, and/or three years than individuals whose levels are comparable to or below the control value or exceeding or in the lower range of control values. The extent of the difference between the test subject's ApoA1 exchange rate and control value is also useful for characterizing the extent of the risk and thereby determining which individuals would most greatly benefit from certain aggressive therapies. In those cases, where the control value ranges are divided into a plurality of groups, such as the control value ranges for individuals at high risk, average risk, and low risk, the comparison involves determining into which group the test subject's level of the relevant risk predictor falls.

In certain embodiments, the subject's ApoA1 exchange rate is compared to a threshold value (e.g., predetermined by assessing a population of patients) in order to determine if the subject has or at risk for a major adverse cardiac event or cardiovascular disease. In some embodiments, the threshold value is 1.0 or less. In other embodiments, the threshold value is 0.9 or less; 0.85 or less; 0.8 or less; 0.7 or less, or 0.6 or less. In certain embodiments, the subjects ApoA1 exchange rate is normalized to a serum pool composed of serum from healthy individuals or individuals without cardiovascular disease (e.g., prior to being compared to the threshold value).

EXAMPLES

Example 1

It was previously reported a dual fluorescently labeled apoA1 reporter that that measured apoA1 lipidation with liposomes and cultured cells (13). This reporter has one lipid-sensitive fluorophore (NBD), and one lipid-insensitive fluorophore (Alexa 647), such that the ratio of fluorescent emission is an indicator of apoA1 lipidation, independent of apoA1 concentration.

In this Example, we used this double labeled apoA1 lipidation reporter indicator as a probe to measure the rate of apoA1 exchange into HDL contained within a small volume of whole serum or plasma. High (top 75th percentile vs. bottom 25th percentile) apoA1 exchange rate was associated with decreased incident MACE in 1000 subjects with an odds ratio of 0.49 (C.I=0.33-0.71), after adjusting for age, sex, traditional risk factors, and HDL-C (p=0.0002).

Methods

Human Samples

Human fasting blood was obtained from healthy volunteers not taking lipid lowering medication under an IRB approved protocol. Blood was processed into serum or plasma fractions. Human serum samples from a Cleveland Clinic catheterization lab cohort or outpatient cohort were obtained under an IRB approved protocols. All subjects gave written informed consent.

ApoA1 Exchange Reporter

Human apoA1 was purified from HDL as previously reported. The lipid free apoA1 was doubly-labeled on free amines with NBD (nitrobenzoxadiazole), whose fluorescence increases in a hydrophobic environment, and Alexa647. Human apoA1 was dissolved in 0.1M sodium bicarbonate buffer and incubated with a 8:2:1 dye:protein mole ratio of NBD chloride (Molecular probes, dissolved in DMSO) and Alexa 647 carboxlic acid succinimidyl ester (Molecular Probes, dissolved in DMSO) at for 1 hour at room temperature. The reaction was stopped by adding 0.1 ml of freshly prepared 1.5M hydroxylamine, pH8.5, and further incubation for 1 hour. The conjugate was purified by extensive dialysis.

ApoA1 Exchange Rate Assay

The standard protocol of the apoA1 exchange rate (AER) assay is performed by adding 5 ug of the apoA1 exchange reporter to 85 ul of phosphate buffered saline (PBS) in a 96 well dish. Then 5 ul of a standard pool of human serum, or 5 ul of a test human serum or plasma samples is added to each well. The plate is put into a 96 well fluorescent plate reader set at 37° C., and mixed for 15 seconds. The NBD (460 nm excitation, 540 nm emission) and Alexa 647 (640 nm excitation, 670 nm emission) fluoresce is read at 1 minute intervals. The apoA1 exchange rate is calculated by using linear regression of the NBD/Alexa647 ratio (excluding the non-linear first 10 minutes). In order to account for inter assay variance, the apoA1 exchange rate of each sample is normalized by dividing by the mean of the exchange rate of triplicate samples of the pooled serum standard.

Results

ApoA1 Exchange Reporter Only Exchanges onto HDL in Human Serum.

Figure 1:
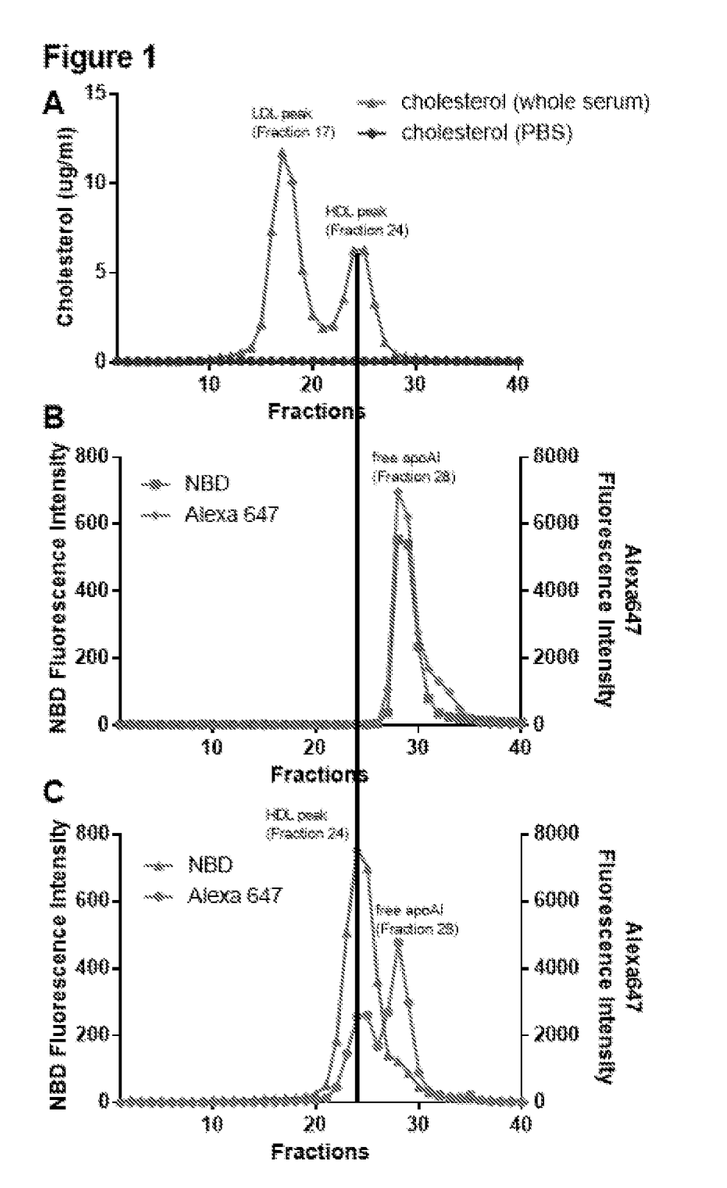
FIG. 1. ApoA1 exchange reporter only exchanges into HDL fraction in human serum. 100 μg apoA1 exchange reporter was incubated with 100 μl PBS or normal human serum in a total volume of 300 μl at 37° C. for 1 hour, and 100 ul of the product was size fractioned by FPLC using a Superose 6 (10/300 GL) column and 0.5 ml fractions were collected. The cholesterol concentration was measured in each fraction (A), with the LDL-C peak at fraction 17 and HDL-C peak at fraction 24. The fluorescent intensities of NBD (excitation 460 nm, emission 540 nm) and Alexa647 (excitation 640 nm, emission 670 nm) were measured in each fraction for the apoA1 exchange reporter incubated with PBS only (B), or incubated with human serum (C). The apoA1 exchange reporter NBD and Alexa647 fluorescence peaks were in the lipid-free apoA1 fraction 28 in PBS group. After apoA1 exchange reporter incubation with human serum, there were NBD fluorescence peak co-migrates with the HDL-C fraction 24, but not in the LDL-C fraction 17.
Figure 2:
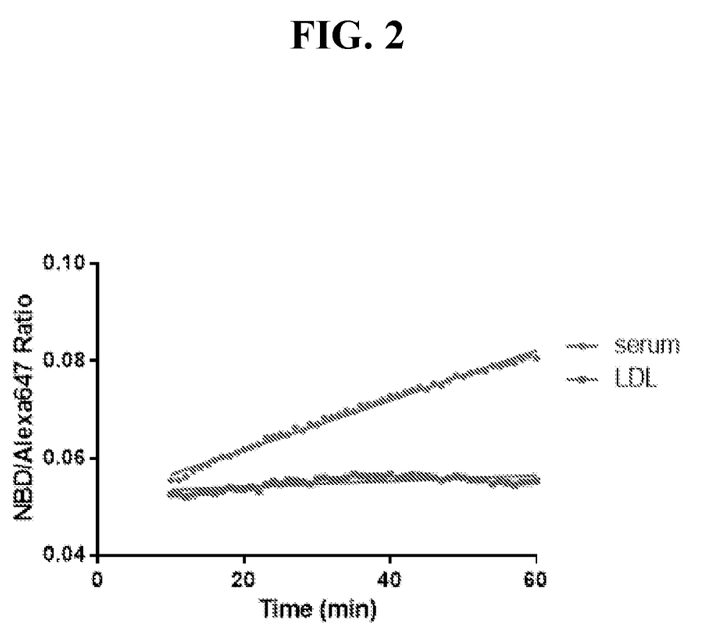
FIG. 2. ApoA1 exchange reporter does not react with isolated human LDL. 5 μg apoA1 exchange reporter was added to 85 μl PBS in a 96 well dish, then 8 μg isolated human LDL or 5 μl human serum was added to different wells. The plate was put into a spectrophotometer set at 37° C., with the intensity of NBD (excitation 460 nm, emission 540 nm) and Alexa647 (excitation 640 nm, emission 670 nm) read at 1 min interval for 1 hr. The ratio of NBD/ALexa647 was calculated (excluding the non-linear first 10 minutes). Incubation of the apoA1 exchange reporter with LDL did not appreciably increase the NBD/Alexa647 ratio over time.

The apoA1 exchange reporter (100 ug) was incubated with 100 ul human serum for 1 hour at 37° C. 100 ul of the product was size fractioned by FPLC using a Superose 6 (10/300 GL) column (BioRad). The fluorescence in both channels was measured in each fraction (FIG. 1). Before incubation with serum, the apoA1 exchange reporter NBD and Alexa 647 peaks were in fraction 28, where lipid-free apoA1 runs. After incubation with serum, the NBD peak was in fraction 24, co-migrating with the HDL-C peak, and there was no peak co-migrating with LDL in fraction 17. There were two Alexa 647 peaks, one in the HDL fraction, and one in the lipid-free apoA1 peak. To confirm that the apoA1 exchange reporter only exchanges into HDL and not LDL, we incubated it with serum or 8 ug protein of isolated human LDL using our standard assay conditions. There was negligible increase of the NBD/Alexa 647 ratio with human LDL vs. serum (FIG. 2).

Characteristics of apoA1 Exchange Rate Assay

Figure 3:
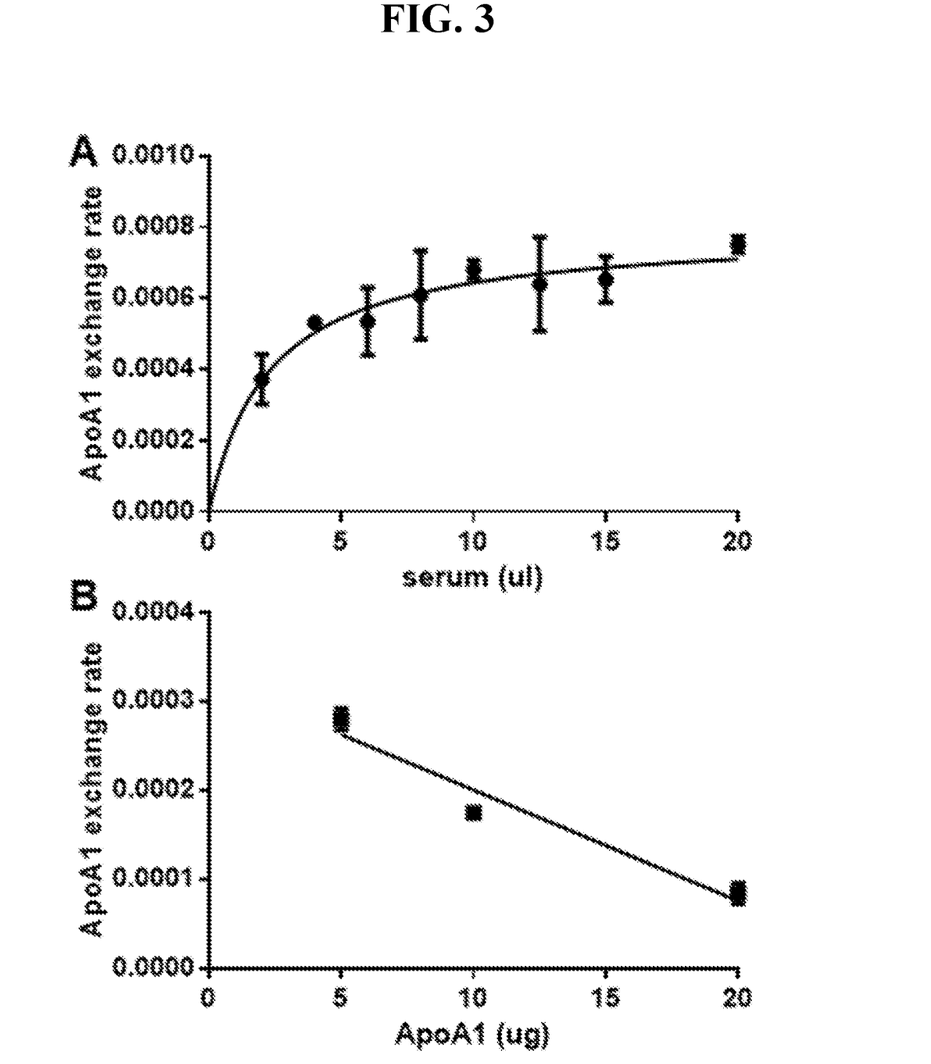
FIG. 3. Dose responses of human serum and apoA1 exchange reporter in apoA1 exchange assay. A. ApoA1 exchange rate measured with the condition of 5 μg apoA1 exchange reporter with different indicated volumes of human serum. B. ApoA1 exchange rate measured with 5 μl human serum with indicated doses of apoA1 exchange reporter. (N=6; mean+SD).

Dose responses for both the apoA1 exchange reporter and serum were performed (FIG. 3 A. B). The apoA1 exchange reporter was varied between 2.5 and 20 ug keeping the serum constant at 5 ul. The reaction rate starts to plateau above 5 ug apoA1 exchange reporter, thus we used 5 ug in our standard assay. 5, 10, or 20 ul of serum was used keeping the apoA1 exchange reporter constant at 5 ug. The highest rate was observed using 5 ul of serum, which was then used in our standard assay.

Figure 4:
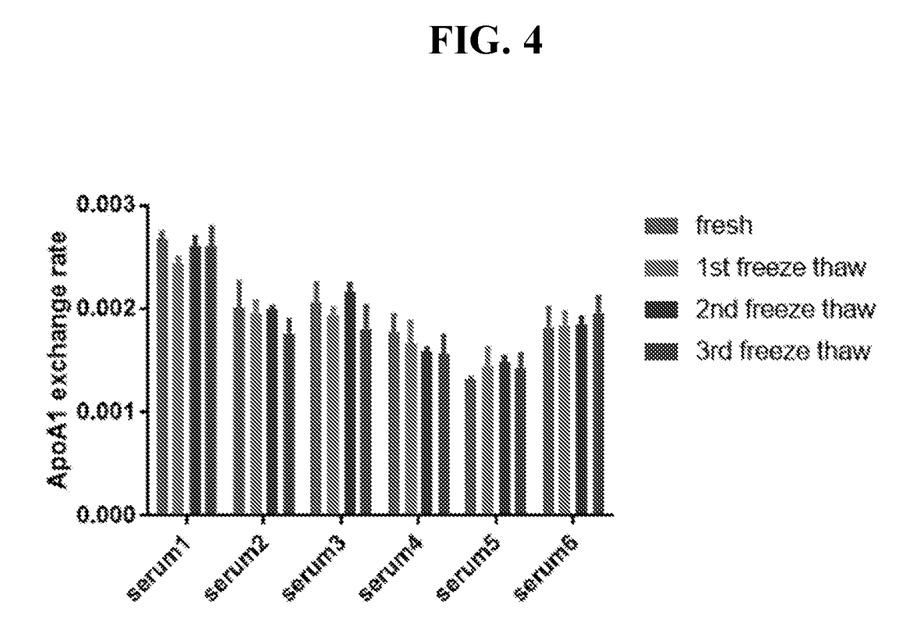
FIG. 4. Freeze-thaw cycles have no effect on apoA1 exchange rate. ApoA1 exchange rate assay was performed with six control serum samples obtained freshly, and with the same samples subjected to 1-3 freeze-thaw cycles using dry ice and a 37° C. water bath. The apoA1 exchange rate did not change significantly when samples underwent 1-3 freeze-thaw cycles (N=3; mean+SD; P>0.05 by ANOVA posttests).

We compared 6 control serum samples from healthy donor volunteers obtained fresh vs. the same samples subjected to 1-3 cycles of freeze-thaw using dry ice and a 37° water bath. There was no loss of apoA1 exchange rate upon freeze-thaw (FIG. 4).

Figure 5:
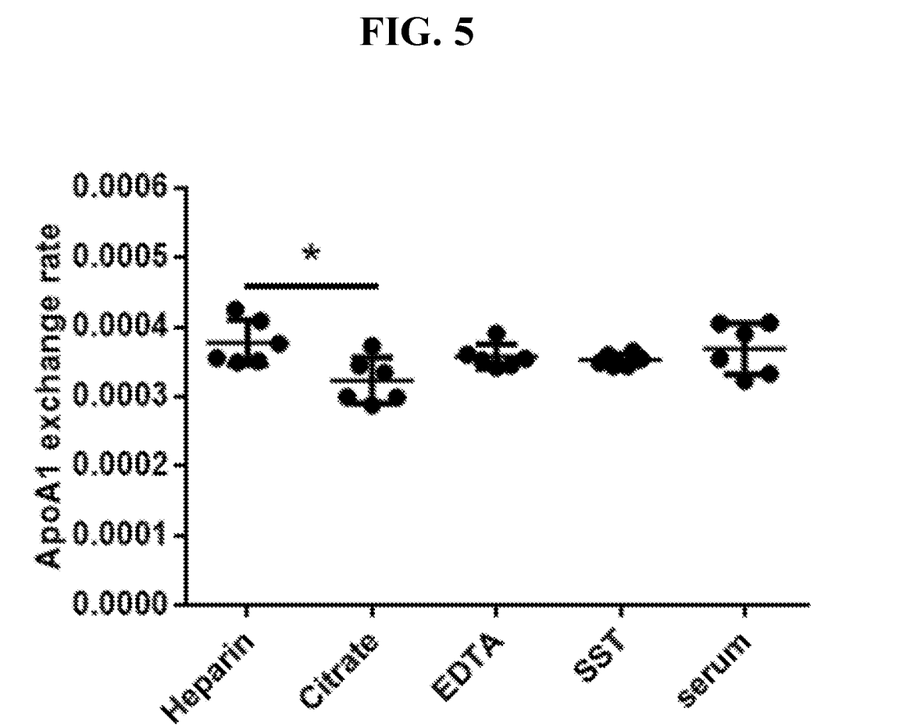
FIG. 5. ApoA1 exchange rate in different preparations of plasma and serum. ApoA1 exchange rate assay was performed with different sample preparation from the same control donor, which were heparin plasma, sodium citrate plasma, EDTA plasma, serum from serum separator tubes, and serum from the clot activator tube (N=6; mean+SD; *P<0.05 by ANOVA posttest).

Using one control donor blood sample, we prepared two types of serum (red top clot activator Vacutainer tube BD #367820 or gold top serum separator SST Vacutainer tube BD #367986) and three types of plasma (EDTA Vacutainer tube BD #366643, lithium heparin Vacutainer tube BD #5014830, and sodium citrate Vacutainer tube BD #369714). Six replicate apoA1 exchange rate assays were performed for each sample (FIG. 5), and all samples gave similar rates, except for the sodium citrate that yielded slightly but significantly lower exchange rate by ANOVA (p<0.05 vs. all other samples). The apoA1 exchange rate coefficient of variation for the sextuplet assays varied between 2.41 to 10.14%.

ApoA1 exchange rate inter-day coefficient of variations were calculated using 12 serum samples assayed on 12 different days that yielded a range between 4.58 to 11.76%, with a mean of 7.52.

Figure 6:
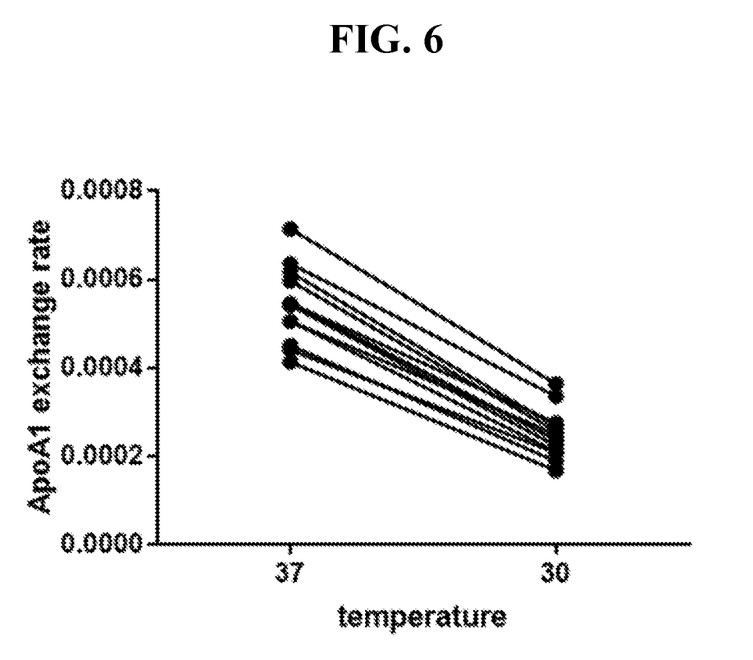
FIG. 6. ApoA1 exchange rate is temperature dependent. ApoA1 exchange rate assay was performed with 12 control serum samples at 37° C. or 30° C., and apoA1 exchange rate was faster at 37° C.
Figure 7:
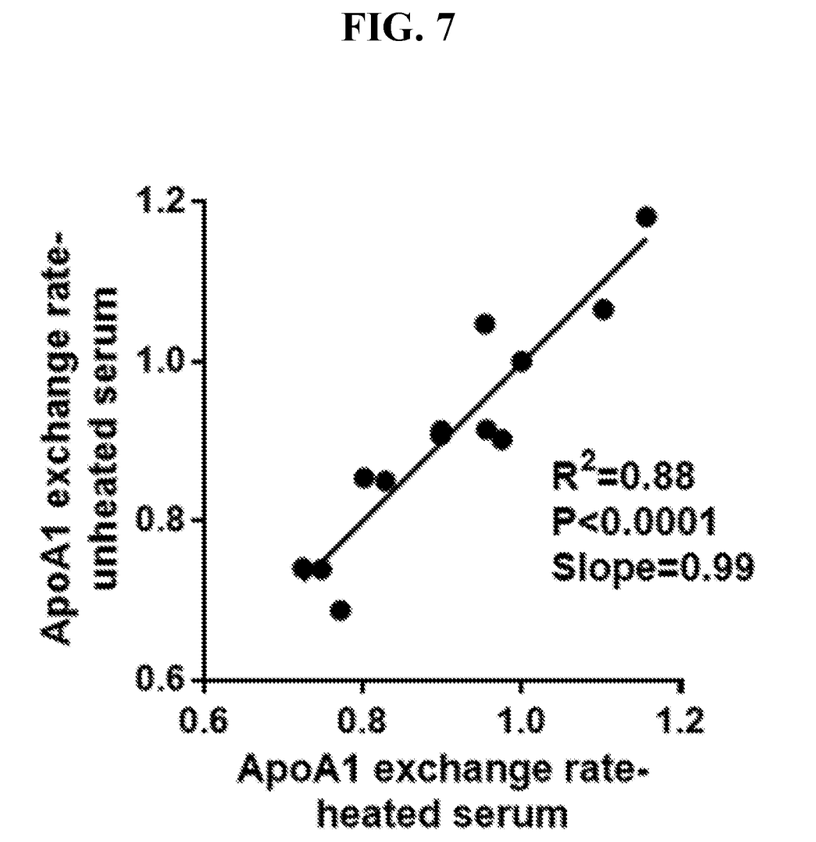
FIG. 7. ApoA1 exchange rate is not inhibited by prior serum heat inactivation. ApoA1 exchange rate assay was performed with 12 control serum samples unheated or heated at 56° C. for 1 hour, and apoA1 exchange rate was not inhibited by serum heat inactivation.

To determine if the apoA1 exchange rate is temperature dependent we compared rates at 37 and 30° C. for 12 serum samples, and we observed faster rates at 37° C. (FIG. 6). To determine if apoA1 exchange rate was mediated by plasma enzymes we compared 12 untreated serum with the same samples after heat-treatment at 56° C. for 1 hour. There was no effect of heat treatment on the apoA1 exchange rate (FIG. 7, r2=0.88, slope=0.99).

Correlation of apoA1 Exchange Rate with Cholesterol Efflux Capacity

Figure 8:
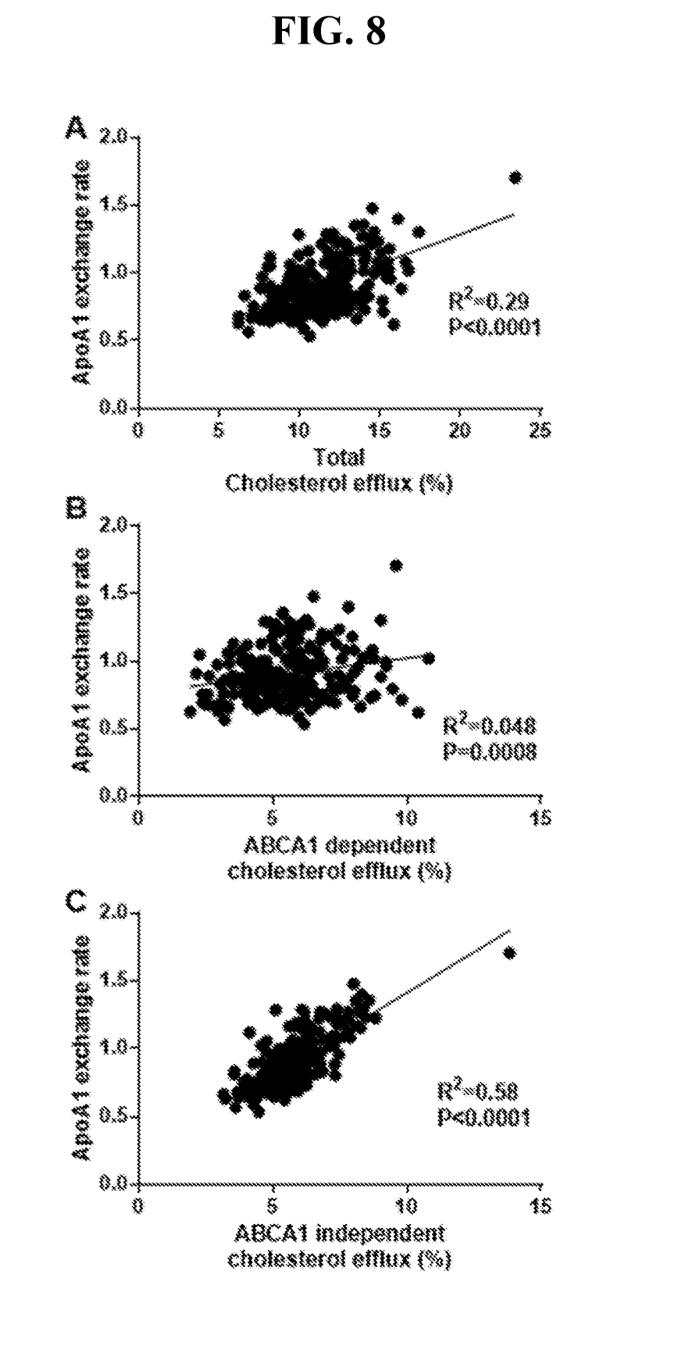
FIG. 8. Correlation of apoA1 exchange rate to cholesterol efflux capacity. ApoA1 exchange rates were assayed in 279 human serum samples from outpatients, and the total cholesterol efflux capacity to the same samples (2% apoB-depleted serum, v/v) was measured in RAW264.7 cells with ABCA1 induction (A). The ABCA1 dependent cholesterol efflux capacity (B) was calculated as the difference between total efflux capacity (A) and cells without ABCA1 induction (C). Correlation of apoA1 exchange rate to cholesterol efflux capacity was analyzed using linear regression, and the best fit was with the ABCA1 independent efflux capacity.

We obtained 279 human serum samples from an outpatient clinic and assessed cholesterol efflux capacity using cholesterol labeled RAW264.7 macrophages. We measured apoA1 exchange rate in these samples and the correlation coefficient r2 values with total efflux capacity, ABCA1-dependent efflux capacity, and ABCA1-independent efflux capacity were 0.29, 0.048, and 0.58, respectively (FIG. 8). Thus, the apoA1 exchange assay best correlates with the ABCA1-independent efflux acceptor activity.

High apoA1 exchange rate is associated with decreased incident major adverse cardiovascular events (defined as death, nonfatal myocardial infarction, or nonfatal stroke, MACE) ApoA1 exchange rates were assayed in 997 serum samples obtained from a Cleveland Clinic cardiac catheterization cohort. We correlated apoA1 exchange rates with total cholesterol, LDL-C, HDL-C, triglycerides, Lp(a), and apoA1 levels (Table 1).

TABLE 1

Correlation of apoA1 exchange rate to blood lipid profiles in 997 catheterization lab subjects.

|  | r | P value |
| --- | --- | --- |
| TC | 0.085 | 0.007 |
| LDL-C | 0.044 | 0.169 |
| HDL-C | 0.582 | <0.0001 |
| TG | −0.320 | <0.0001 |
| Lp(a) | 0.077 | 0.015 |
| apoA1 | 0.558 | <0.0001 |

Figure 9:
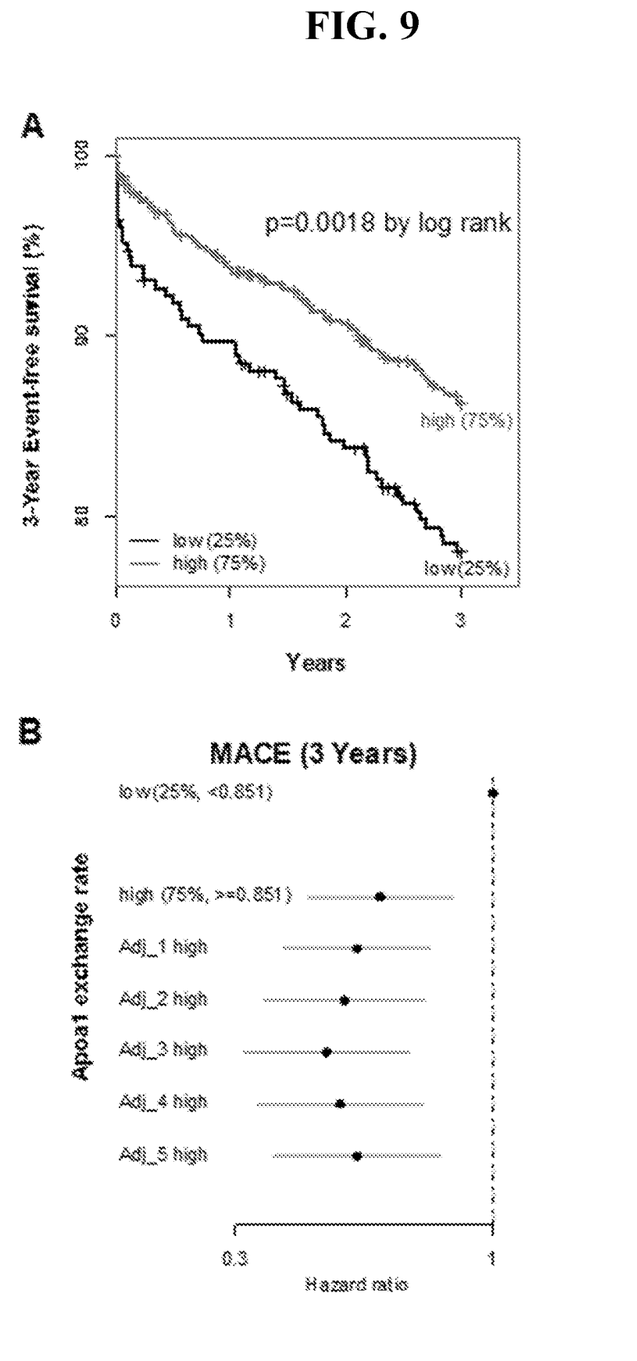
Figure 10:
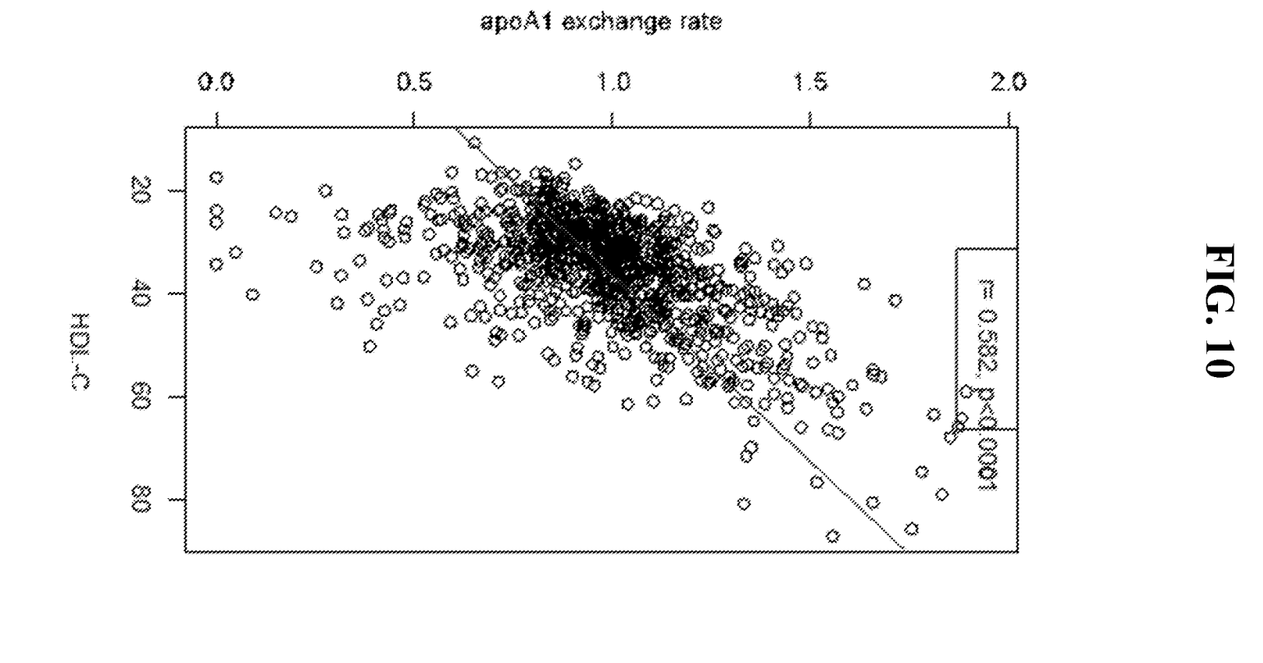
FIG. 10 shows that there are many samples that fall beneath the line with lower apoA1 exchange than expected vs. HDL-C levels, and these are the individuals who are at increased risk for future MACE.

The best correlations were observed for HDL-C and apoA1 (r=0.58 and 0.56, respectively), and an inverse correlation was observed for triglycerides (r=−0.32). MACE-free survival was followed for 3 years in quartiles of apoA1 exchange rates. The lowest quartile the most rapid event rate, but since the other quartiles did not follow in rank order we divided the sample into low and high apoA1 exchange rate groups (bottom 25th and top 75th percentile, respectively). A Kaplan-Meier plot showed significantly faster progression to MACE in the low apoA1 exchange rate group (FIG. 9A, p=0.018). In fact, the difference between these curves was most pronounced at the earliest time points, indicating that this assay may be clinically useful to make decisions for progressive interventions. We compared Hazard Ratio (HR) for MACE in the high vs. low apoA1 exchange rate groups unadjusted, and adjusted for demographic and cardiovascular risk factors (FIG. 9B, Table 2).

TABLE 2

Hazard ratios (HR) for high vs. low apoA1 exchange rate and MACE after adjustments described in the legend for FIG. 9B.

|  | MACE | | |
| --- | --- | --- | --- |
|  | HR low exchange rate | HR high exchange rate | P value |
| Unadjusted | 1 | 0.59(0.42-0.82) | 0.0020 |
| Adjustment 1 | 1 | 0.53(0.38-0.75) | 0.0003 |
| Adjustment 2 | 1 | 0.50(0.34-0.72) | 0.0002 |
| Adjustment 3 | 1 | 0.46(0.31-0.67) | <0.0001 |
| Adjustment 4 | 1 | 0.49(0.33-0.71) | 0.0002 |

TABLE 2-continued

Hazard ratios (HR) for high vs. low apoA1 exchange rate and MACE after adjustments described in the legend for FIG. 9B.

|  | MACE | | |
| --- | --- | --- | --- |
|  | HR low exchange rate | HR high exchange rate | P value |
| Adjustment 5 | 1 | 0.52(0.36-0.78) | 0.0012 |
| # Events/ subjects (%) | 52/249 (20.9) | 97/748 (12.9) |  |

There was a significant decrease in HR in the unadjusted and all adjusted models, even after adjustment for HDL-C (HR=0.49) or apoA1 (HR=0.52). Thus, this simple assay using small volumes of serum can discriminate among patients most likely to progress with a recurrent cardiovascular event.

REFERENCES

1. Gordon et al., Am J Med. 1977; 62:707-14.
2. Assmann et al., Atherosclerosis. 1996; 124 Suppl:S11-20.
3. Boden et al., N Engl J Med. 2011; 365:2255-67.
4. Schwartz et al., N Engl J Med. 2012; 367:2089-99.
5. Barter et al., N Engl J Med. 2007; 357:2109-22.
6. Lincoff et al., N Engl J Med. 2017; 376:1933-1942.
7. Voight et al., Lancet. 2012; 380:572-80.
8. Khera et al., N Engl J Med. 2011; 364:127-35.
9. Rohatgi et al., N Engl J Med. 2014; 371:2383-93.
10. Saleheen et al., Lancet Diabetes Endocrinol. 2015; 3:507-13.
11. Borja et al., PLoS One. 2013; 8:e71541.
12. Borja et al., J Lipid Res. 2015; 56:2002-9.
13. Wang et al., Arterioscler Thromb Vasc Biol. 2013; 33:1197-205.

ADDITIONAL REFERENCES

1. Wang et al., Arterioscler Thromb Vasc Biol. 2013, 33:1197-205.
2. Cavigiolio et al., J Biol Chem. 2010, 285):18847-57.
3. Borja et al., PLoS One. 2013, 8:e71541.
4. Borja et al., J Lipid Res. 2015, 56:2002-9.
5. Heier et al., Cardiovasc Diabetol. 2017; 16:85.
6. Block et al., Prostaglandins Leukot Essent Fatty Acids. 2017, 126:25-31.
7. Sarzynski et al., Arterioscler Thromb Vasc Biol. 2018, 38:943-952.
8. Handa et al., Biochemistry. 2015, 54:1123-31.
9. United States Patent Application Publication Pub. No.: US 2016/0305967

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of detecting lipid-free apoA1 reporter molecules in a serum sample from a human subject comprising:
   a) contacting a serum sample from a human subject with lipid-free apoA1 reporter molecules,
   wherein said serum sample comprises HDL molecules and LDL molecules,
   wherein said lipid-free apoA1 reporter molecules each comprise at least a portion of human ApoA1 that is labeled with: i) nitrobenzoxadiazole, a lipid sensitive label whose fluorescence increases in a hydrophobic environment, and ii) a lipid insensitive fluorescent label; and
   b) detecting: i) a first signal from said lipid sensitive label, and ii) a second signal from said lipid insensitive label, wherein said lipid-free apoA1 reporter molecules exchange into said HDL molecules in said serum sample at a rate detectable by said first and second signals together.

2. The method of claim 1, further comprising: generating a report that graphically displays said subject's ApoA1 exchange rate.

3. The method of claim 2, wherein said report graphically displays said subject's ApoA1 exchange rate as less than said a threshold value of 0.85.

4. The method of claim 3, wherein said subject's ApoA1 exchange rate is presented in a column indicative of being lower than said threshold value.

5. The method of claim 3, wherein said subject's ApoA1 exchange rate is presented in a color indicative of being lower than said threshold value.

6. The method of claim 2, wherein said report graphically displays:
   i) said subject's ApoA1 exchange rate in said sample as:
      i) lower than a control value, and/or ii) lower than a threshold value of 0.85; and
   ii) said subject's risk of a major adverse cardiac event (MACE) and/or cardiovascular disease being higher than normal.

7. The method of claim 6, wherein said subject's ApoA1 exchange rate is presented in a column indicative of being lower than said control value.

8. The method of claim 6, wherein said subject's ApoA1 exchange rate is presented in a color indicative of being lower than said control value.

9. The method of claim 6, wherein said control value is based on the average ApoA1 exchange rate from a plurality of healthy individuals or a plurality of individuals without cardiovascular disease.

* * * * *